United States Patent
Witt-Enderby et al.

(10) Patent No.: US 8,618,083 B2
(45) Date of Patent: Dec. 31, 2013

(54) COMBINATION HORMONE REPLACEMENT THERAPY (HRT) AND MELATONIN TO PREVENT AND TREAT MAMMARY CANCER

(75) Inventors: Paula A Witt-Enderby, Allegheny County, PA (US); Vicki L Davis, Butler County, PA (US)

(73) Assignee: Duquesne University of the Holy Spirit, Pittsburgh, PA (US)

( * ) Notice: Subject to any disclaimer, the term of this patent is extended or adjusted under 35 U.S.C. 154(b) by 311 days.

(21) Appl. No.: 12/804,341

(22) Filed: Jul. 20, 2010

(65) Prior Publication Data
US 2011/0028439 A1    Feb. 3, 2011

Related U.S. Application Data

(60) Provisional application No. 61/273,165, filed on Jul. 31, 2009.

(51) Int. Cl.
*A01N 45/00*    (2006.01)
*A61K 31/56*    (2006.01)

(52) U.S. Cl.
USPC ............. 514/170; 514/169; 514/171

(58) Field of Classification Search
None
See application file for complete search history.

(56) References Cited

PUBLICATIONS

Cagnacci et al. Different circulatory response to melatonin in postmenopausal women without and with hormone replacement therapy J Pineal Res. Oct. 2000; 29(3):152-8 (abstract).*

Cagnacci et al. "Effect of exogenous melatonin on vascular reactivity and nitric oxide in postmenopausal women: role of hormone replacement therapy", Clin Endocrinol (Oxf) Feb. 2001;54(2):261-6 (abstract).*

Writing Group for the Women's Health Initiative Investigators (2002). "Risks and Benefits of Estrogen Plus Progestin in Healthy Postmenopausal Women: Principal Results From the Women's Health Initiative Randomized Controlled Trial". JAMA 288 (3): 321-333. doi:10.1001/jama.288.3.321. PMID 12117397.*

Writing Group . . . , "Risks and Benefits of Estrogen Plus Progestin . . . ," Journal of the American Medical Association, vol. 288, No. 3, pp. 321-333 (2002).

* cited by examiner

*Primary Examiner* — James D Anderson
*Assistant Examiner* — William Lee
(74) *Attorney, Agent, or Firm* — Barbara E. Johnson, Esq.

(57) ABSTRACT

A combination hormone and melatonin therapy is provided to reduce the risk of developing, or to reduce the severity of, breast cancer by administering at least one estrogen hormone and optionally at least one progesterone-receptor-binding compound or composition and melatonin together, preferably at normal bed time.

1 Claim, 4 Drawing Sheets

COMBINATION HORMONE REPLACEMENT THERAPY (HRT) AND MELATONIN TO PREVENT AND TREAT MAMMARY CANCER

CROSS-REFERENCE TO RELATED APPLICATION

This application claims priority to, and incorporates herein by reference, U.S. Provisional Patent Application No. 61/273,165 filed Jul. 31, 2009.

BACKGROUND OF THE INVENTION

1. Field of the Invention

With an emphasis on women's overall health, the invention pertains to improved prevention and treating agents, and methods for preventing and treating, mammary cancer.

2. Description of Related Art

In addressing mammary (breast) cancer, it is important to address a woman's overall health besides just the prevention or treatment of cancer. The ability of peri-menopausal women to treat menopausal symptoms while also decreasing their risk of breast cancer is important in improving quality of life as well as in reducing the risk of other age-related diseases. As hormone replacement therapy is currently recommended only for short-term use for women with severe menopausal and peri-menopausal symptoms, many women struggle through problems including but not limited to hot flushes, vaginal dryness, irritability, and incontinence. Estrogen therapy has been the most effective therapy to date to help with all those symptoms as well as in protecting against osteoporosis.

At the same time, prevention and treatment of breast cancer is important in improving both health and quality of life. Certain treatments which do not fall within the typical bounds of traditional chemotherapy have shown significant promise, such as the oral administration of melatonin. Melatonin was, prior to the present invention, known to exhibit distinctive anti-mammary-cancer effects, and previous studies have shown that enhancing the nocturnal surge in melatonin, by administering melatonin at bedtime or during the night, has been more protective against the development of mammary cancer than supplementing melatonin in a continuous manner. There has been a general consensus in the mammary cancer field, however, that melatonin itself is not an adequate preventive or treatment for mammary cancer, despite its positive effects. Even though other recent strides in breast cancer treatment have been favorably impressive a need still remains for a particular therapy which can both prevent or treat mammary cancer at the same time the treatment reduces or eliminates the symptoms of peri-menopause or menopause, ideally while presenting risks or side effects within the general bounds of those of melatonin. Despite this need, the prevailing wisdom at this writing (not including the present invention) is that treating menopause, and preventing or treating breast cancer, are separate disciplines. However, logically, if there were a safe and effective way of treating menopause and at the same time preventing or treating breast cancer in the same therapeutic regimen, such a therapy would represent a significant—even historic—advance in women's health care.

SUMMARY OF THE INVENTION

In order to meet this need, the present combination therapy both treats the symptoms of peri-menopause or menopause and simultaneously acts to prevent or to treat mammary cancer in a patient—particularly (but not necessarily only) in a female patient aged 40 or older. The combination therapy includes hormone replacement therapy (HRT) and melatonin as discussed below. (HRT is sometimes revised to MRT in current usage, signifying "menopause replacement therapy" inasmuch as the term HRT is not specific for women or menopausal symptoms. Having said that, to the end that the present therapy can be administered to HRT both the HRT and MRT terms are apropos.) In giving both HRT and melatonin together, it is possible to reduce mammary cancer incidence or to treat existing mammary cancer and also to treat the symptoms of peri-menopause or menopause, at the same time, and both to a significant degree. The HRT typically includes an estrogen at about the currently recommended dose, a progesterone-receptor-binding compound at about half the currently recommended dose, and melatonin at the currently recommended dose for melatonin administered alone, but with the melatonin administered at bedtime or during the night.

BRIEF DESCRIPTION OF THE DRAWING(S)

DETAILED DESCRIPTION OF THE INVENTION

Figure 1A:
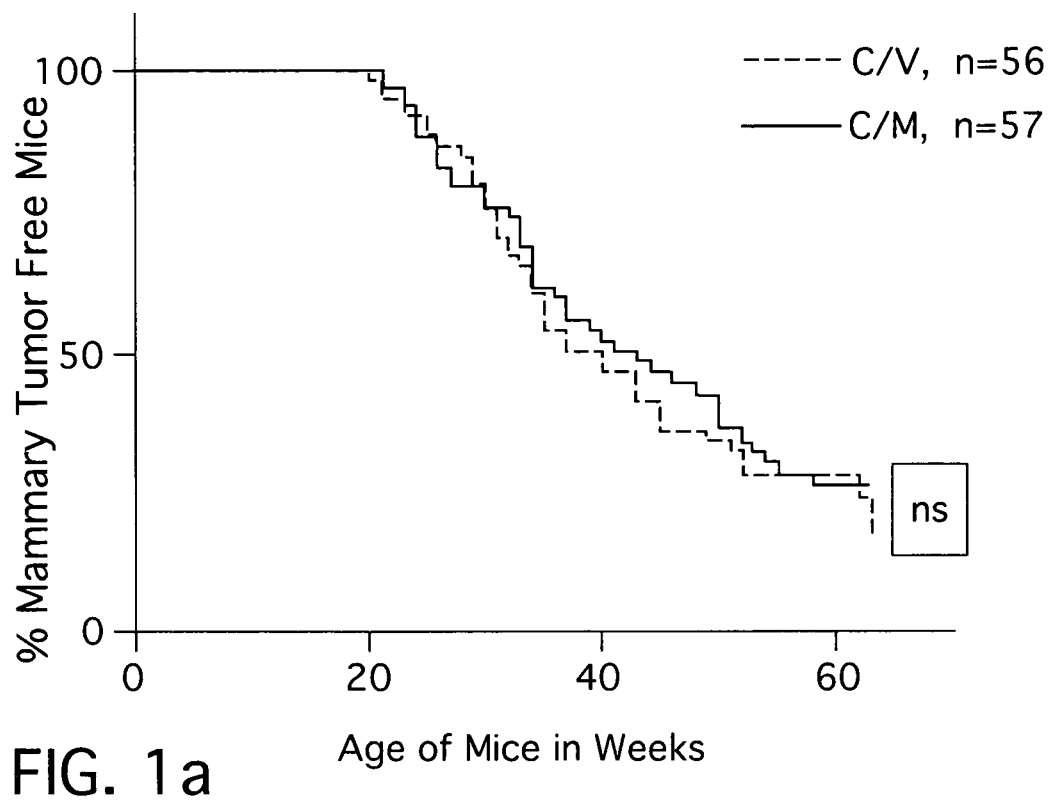
FIG. 1a is a line graph showing age of primary mammary tumor onset and incidence between control (C/V) vs. melatonin (C/M) groups.
Figure 1B:
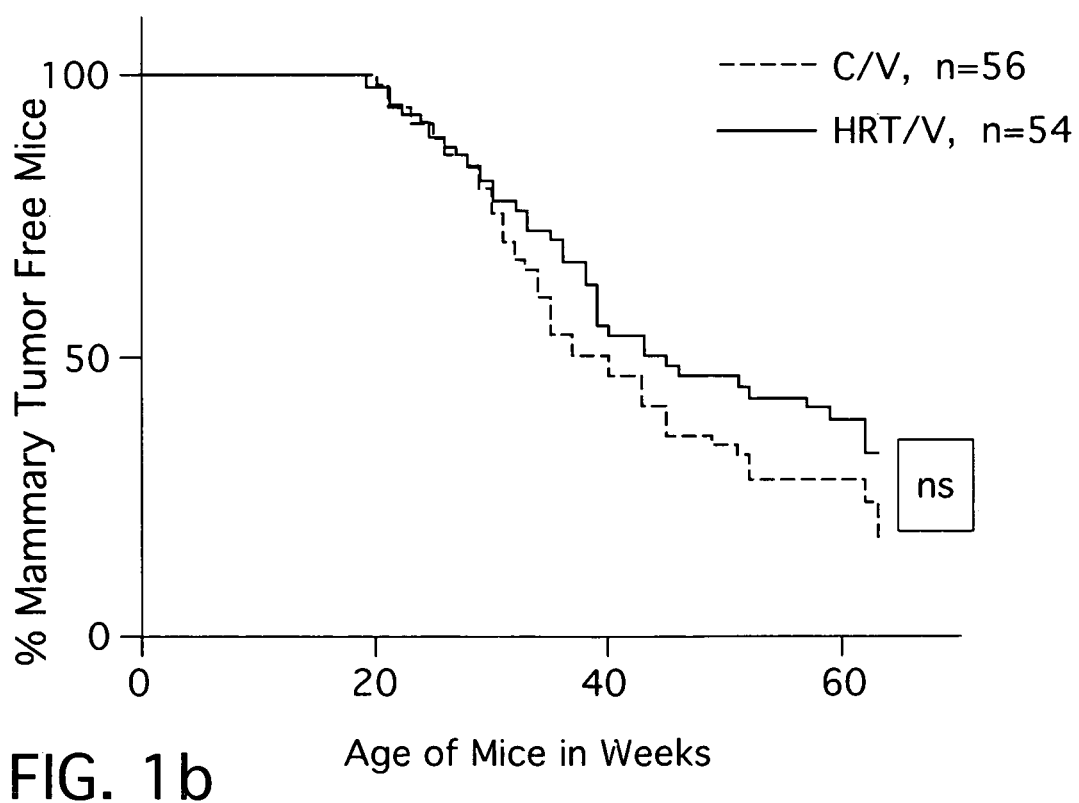
FIG. 1b is a line graph showing age of primary mammary tumor onset and incidence between control vs. HRT (HRT/V) groups.
Figure 1C:
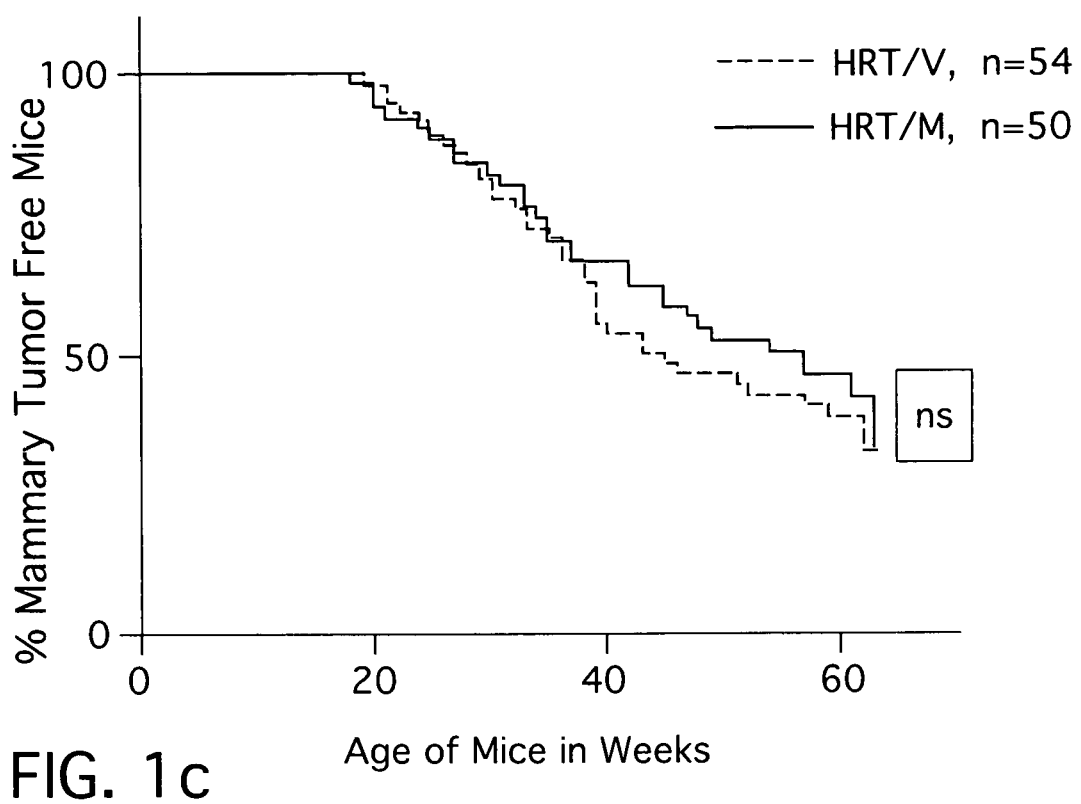
FIG. 1c is a line graph showing age of primary mammary tumor onset between HRT vs. HRT plus melatonin (HRT/M) groups.
Figure 1D:
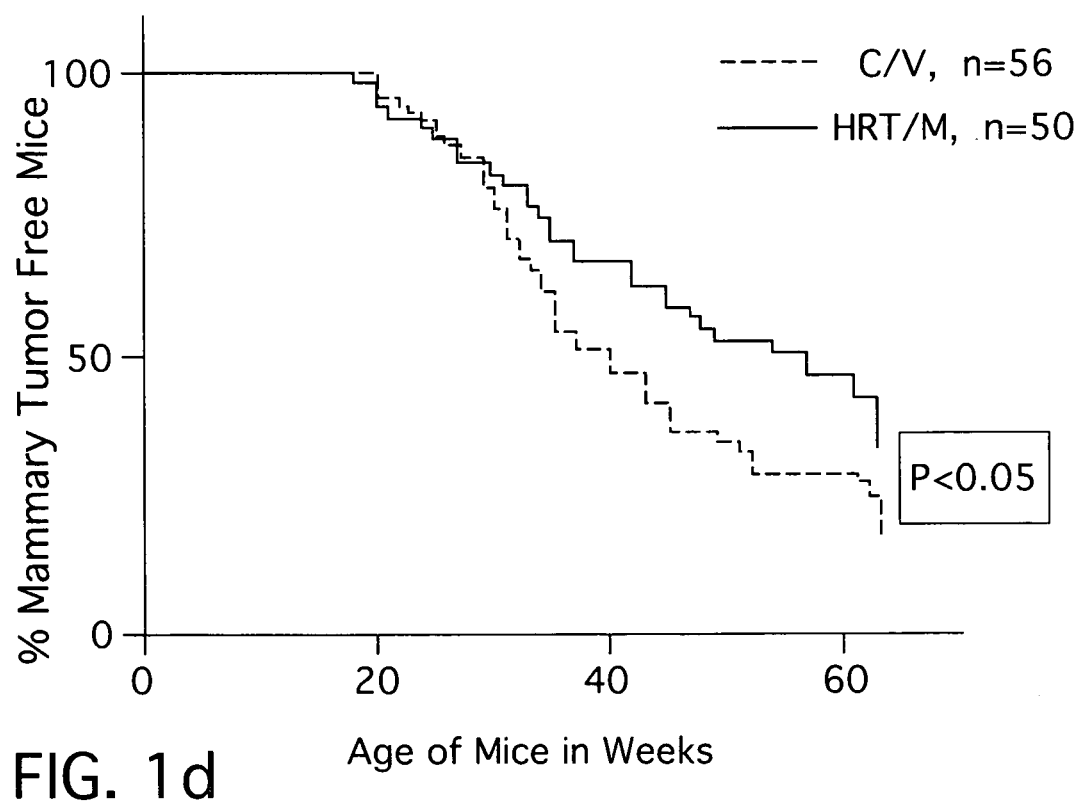
FIG. 1d is a line graph showing age of primary mammary tumor onset between control vs. HRT plus melatonin (HRT/M) groups.

The present combination therapy both treats the symptoms of peri-menopause or menopause and simultaneously acts to prevent or to treat mammary cancer in a patient—particularly (but not necessarily only) in a female patient aged 40 or older. The combination therapy includes hormone replacement therapy (HRT) and melatonin as discussed below. In giving both HRT and melatonin together, it is possible to reduce mammary cancer incidence or to treat existing mammary cancer and also to treat the symptoms of peri-menopause or menopause, at the same time, and both to a significant degree. The HRT typically includes an estrogen at about the currently recommended dose, a progesterone-receptor-binding compound at about half the currently recommended dose, and melatonin at the currently recommended dose for melatonin administered alone, but with the melatonin administered at bedtime or during the night.

To simplify compliance, the combined active agents may be compounded together in an oral dosage form intended for administration at bedtime. A typical oral dosage form could contain 0.5 mg 17β-estradiol ($E_2$), 50 mg of progesterone ($P_4$) and 5 mg melatonin, together with customary pharmaceutically acceptable excipients and diluents, in a form typically intended for oral administration such as a tablet, a capsule, a caplet, a lozenge, a fast-dissolve strip, or a piece of chewing gum, without limitation. The oral dosage form may also be a solution, containing one or more of the above-described active agents or other similar active agents described below; if the active agents are in separate solutions the combination therapy may be implemented by administering one or more solutions to the patient at the same time. The combined active agents may also be used as constituents or additives in food supplements including but not limited to food bars and supplement drinks, although most usually the combined active agents are given with minimized if any additional calories due to the optimal bedtime administration of at least the melatonin component. Daily dosage variations for the above-described oral dosage form include the combination of 0.1-0.9 mg 17β-estradiol ($E_2$) with 10-90 mg of progesterone ($P_4$) and 1-9 mg melatonin, more preferably 0.2-0.9 mg 17β-estradiol ($E_2$) with 20-80 mg of progesterone ($P_4$) and 2-8 mg melatonin, and most preferably 0.4-0.6 mg 17β-estradiol ($E_2$) with 40-60 mg of progesterone ($P_4$) and 4-6 mg melatonin. Typically these dosages may be adjusted, according to the skill in the art, to accommodate patients whose body weights vary significantly from an average body weight. The active agents of the present invention, as well as their compounding and oral dosage form preparation generally, are already known in the art, and the present invention is directed to the improvement of coadministration of HRT and melatonin in the improved therapies disclosed herein.

The estrogen and progesterone components of the above-described exemplary formulation each represent an active agent chosen from the classes of a) estrogens and b) progesterone-receptor-binding compositions. Estrogens include, without limitation, estradiol, ethinyl estradiol (EE), estriol, estrone, conjugated equine estrogens (CEE) and progesterone-receptor-binding compound include, without limitation, progesterone, medroxyprogesterone acetate; levonorgestrel, norethindrone, norethindrone acetate, norgestimate or other progestins. The term "progesterone-receptor-binding compound" is used to avoid general confusion among the nomenclature of progestins/progesterone, because any compound (or composition) which binds to the progesterone receptor is contemplated for use in the present invention. In the oral formulation, 17β-estradiol, progesterone and melatonin are preferred. The two constituents together may even be "CEE/MPA" (conjugated equine estrogen/medroxyprogesterone acetate) already known in the art, without reducing the progesterone proportionately (because there is no easy way to do so).

As described above, when 17β-estradiol, progesterone and melatonin are administered in the practice of the invention, oral administration and oral dosage forms are advantageous for ease of administration and compliance enhancement. However, the various estrogens, progesterone-receptor-binding compounds (or compositions) and melatonin may be given by a wide variety of routes of administration and their dosage ranges will vary accordingly. A good route of administration for certain estrogens is transdermal (via a patch known in the art) to avoid the hepatic first pass effect and certain resultant metabolites which may themselves promote breast cancer. Synthetic hormones will generally be administered via the oral route. Transmucosal delivery methods (vaginal delivery, sublingual, buccal, etc.) may be used with the present invention, as may implants, parenteral administration, or any other route of administration, with the understanding that for practical simplicity and patient compliance oral administration is generally preferred.

Overall, those skilled in the art understand that in order to reach the therapeutic blood levels expected with administration of 17β-estradiol, progesterone and melatonin described above, adjustment must be made for route of administration and other dosing considerations. The following comments are explanatory and orient the reader to certain considerations already known in the art, to determine dosing by other routes of administration. When given transdermally according to the prior art, 17β-estradiol is administered at 0.025 mg to 0.1 mg per day for Climara (as an nonlimiting example). The prior art Climara Pro HRT patch uses 17β-estradiol at 0.045 mg/day and levonorgestrel at 0.015 mg/day. Other synthetic oral progestins are more potent and absorb better than progesterone so their doses are considerably lower than a comparable progesterone dose. CEE/MPA HRT (oral) currently is given at the recommended lowest dosages of 0.3 mg CEE+1.5 mg MPA. Therefore, reducing even the 0.3/1.5 proportion so that the progesterone approaches half that amount is in keeping with the present invention. PREMPRO® 0.3 mg/1.5 mg therapy consists of a single tablet containing 0.3 mg of the conjugated equine estrogens (CEE) found in Premarin® tablets and 1.5 mg of medroxyprogesterone acetate (MPA) for oral administration. PREMPRO 0.45 mg/1.5 mg therapy consists of a single tablet containing 0.45 mg of the conjugated estrogens found in Premarin tablets and 1.5 mg of medroxyprogesterone acetate for oral administration. Again, these typical dosage forms available at this writing help to illustrate how to implement the present invention with a typical dose of an estrogen accompanied by an approximately half-typical dose of progesterone (or substitute) and to illustrate what "half" means in the context of currently typical therapies and commercial dosage forms for which the invention preferably includes half the typical amount of progesterone or equivalent. PREMPRO 0.625 mg/2.5 mg therapy consists of a single tablet containing 0.625 mg of the conjugated estrogens found in Premarin tablets and 2.5 mg of medroxyprogesterone acetate for oral administration. By taking any of these currently commercial products or their equivalents and reducing the progesterone-receptor-binding compound (composition) to about half, adding melatonin and administering at night, one can practice the present invention. The best iterations are the dedicated dosages forms including a single pill, solution or other construct that is administered to the patient as a single dosage form.

In line with the previous paragraph, when 17β-estradiol and levonorgestrel are combined in a dosage form for the treatment of the present invention, the ratio by weight of 17β-estradiol to levonorgestrel is about 5.5:1 to 6.5:1, preferably about 6:1. However, because the doses of progesterone must be higher than those of synthetic progestins due to absorption issues, when CEE is combined with medroxyprogesterone acetate (MPA) the ratio by weight of CEE to MPA is about 1:2-2.5. Having said that, however, it is possible to practice the invention by taking any typical hormone replacement therapy known in the art at this writing and containing an estrogen or equivalent and a progesterone or equivalent, and roughly halving the dosage of the progesterone or equivalent component.

The estrogen component is usually adjusted relatively higher to give the best relief for women with symptoms and the progestogen also needs to be adjusted to provide more uterine protection. So if just estrogen is given (ERT, or estrogen replacement therapy), for women without a uterus, the dosage can vary without needing to consider the progesterone dose. A common estrogen given for HRT (oral) and oral contraceptives is ethinyl estradiol (EE), such as in femHRT (2.5 mcg EE+0.5 mg norethindrone or 5 mcg EE+1 mg norethindrone). Progesterone is not available as a patch, since the dose of progesterone needs to be higher than progestins since progesterone is less potent. It is available in creams, such as vaginal or other topical creams. Apart from the single dosage form goal for compliance and convenience, the medically optimal way to administer the combinational therapy is to administer 17β-estradiol by patch and progesterone and melatonin orally in a single pill, even though the progesterone-receptor-binding compound may be administered in a cream such as a vaginal cream when desired. In pill form, the progesterone and 17β-estradiol generally have to be micronized to give optimal delivery. A particularly preferred dosage form is therefore a "one tablet" therapy comprising micronized 17β-estradiol plus micronized progesterone plus melatonin for oral administration in either a cyclic or continuous dosing regimen. For example, if a month's aggregation of pills includes hormone free pills to approximate a monthly cycle, the hormone free pills still include the melatonin, and all the pills for administration throughout the cycle are intended for bedtime or nocturnal administration. It should be borne in mind that the addition of nocturnal melatonin allows the dosage of the progestational agent to be reduced below the minimum level required to protect the uterus in the absence of melatonin supplementation.

The melatonin constituent of the present therapy is described herein as being administered "at bedtime" or "at night." These expressions are shorthand for the idea of administering the melatonin to correspond with the sleep cycle of the patient—so for a night shift worker, the administration time for the melatonin should be modified to correspond to his or her actual bedtime (presumably in the morning) because workers exposed to light all night have their biological clocks disrupted. Ideally, then, the melatonin component of the invention is administered to the patient at the same time as the patient will naturally experience his or her own highest natural melatonin levels or at least the beginning of any natural melatonin surge. As described elsewhere herein any dose between 1-9 mg is within the scope of the invention for prevention of breast cancer, with 3-9 mg per day being preferred for prevention, but it should be understood that up to 50 mg melatonin may be indicated for sole or complementary cancer treatment.

Some important variations on the methods and formulations disclosed herein are that a) for certain patients (women lacking a uterus, primarily), the hormone supplementation may at times be estrogen plus melatonin alone, and b) in certain patients who have been diagnosed with breast cancer, the melatonin therapy alone should continue without hormone supplementation until the patient is cancer free. The estrogen and melatonin together may beneficially be given to women without a uterus, because the progestogen component is used in part to protect the uterine tissue during the hormone replacement therapy. Having said that, there will be times when administration of progesterone-receptor-binding component and melatonin alone, without estrogen, will be indicated and this is within the scope of the present invention also. These periodic or midstream alterations in the ongoing dosing of the patient are consistent with the overall goal of supplementing all three of estrogen, progesterone-receptor-binding compound and melatonin at all points in which the patient is a proper recipient of such therapy. This modification is important to understand in the context of the present therapy's being an ongoing therapy for many patients, beneficially being given for years or decades of improved health and quality of life.

Collectively, the results reported in the Examples below, plus other data not reported here, demonstrate not only that all three treatments—melatonin, HRT, and melatonin+HRT—have protective effects on mammary tumor development and/or progression, but that the combination HRT plus melatonin preventive therapy gives new and unexpected results compared to either preventive therapy given alone or even considered for its additive effects in combination. Indeed, in data not reported here it was confirmed that when a half dose of progesterone (compared to recommended current levels) was given with 17β-estradiol and melatonin, the combination prevented unwanted increase in uterine weight despite the progesterone half-dose. Moreover, by reducing progestin to about half of currently recommended levels, the combination HRT plus melatonin therapy not only gave no adverse effects on mammary cancer risk but a beneficial effect was even observed by reducing incidence and delaying tumor onset. In addition, for mammary tumors that did occur, tumor growth and metastatic incidence were also suppressed compared to untreated mice. At a minimum, the data reported below support that by using estrogen and a reduced dose of a progesterone-receptor-binding compound, the adverse effects reported in a 2002 Women's Health Initiative study may be avoided in women by undergoing the present combination therapy. When melatonin was added to the HRT, anti-cancer benefits were detected both in reducing tumor development and in reducing progression (reduced incidence and delayed onset), so that HRT plus melatonin gave better preventive therapeutic effect on breast cancer than either HRT or melatonin administered alone. Therefore, this combination treatment is believed to be important for both the prevention and treatment of breast cancer in animal (mammalian) and human patients. These data are relevant to a common form of breast cancer, HER2+, which is aggressive and relatively more resistant to therapy than most other forms of breast cancer. As a preventive therapy, these data support the conclusion that upon combined administration of HRT and melatonin according to the invention, fewer women will get breast cancer and, for those that do, it will occur at older ages than had the present combination treatment been withheld. Moreover, even if breast cancer were detected while on this combination therapy, the tumors would be less likely to progress to metastatic disease and would do so, if at all, more slowly. Clearly, reducing metastatic disease or delaying its onset while simultaneously ameliorating the symptoms of peri-menopause or menopause, will have dramatic benefits to a woman's survival and overall health, quality of life and life expectancy.

An important side benefit of nocturnal melatonin therapy in the context of this invention is that, in addition to all the other benefits the patient will experience, the patient will also enjoy the profound benefit of improved sleep. Since most peri-menopausal and menopausal women have sleep disturbances from symptoms or from the naturally declining level of melatonin with age, or both, melatonin supplementation reverses these effects and improves sleep both for the patient and for a spouse or partner sleeping next to or near the patient. Melatonin augments the benefits of HRT by stimulating bone formation to prevent and reverse osteoporosis. It is no exaggeration to say that when patients are given the therapy described herein, particularly women over age 40, they experience better sleep, better well-being, better cancer avoidance or at least delayed onset and reduced incidence of breast cancer, reduced or reversed osteoporosis, and amelioration of the myriad of symptoms of menopause and peri-menopause. The inventive combination is so important that it is difficult to envision that its adoption will not be widespread, in part because the patients themselves will demand it.

Certainly the main population intended for the present treatment is the female population. However, even though men are reluctant to agree to administration of estrogen or estrogen/progesterone (or equivalent) female hormones, the present invention does not preclude the administration of the disclosed therapy to men as well as women in circumstances of need (see for example the next paragraph).

As a general consideration, the present invention is optimal for patients having been diagnosed with, or at risk for, estrogen-independent breast cancer. Heretofore there has been a stigma—a de facto taboo—to the administering of estrogen to a breast cancer patient unless the patient has estrogen-independent breast cancer, even though keeping estrogen available usually means that even non-estrogen-independent breast cancer tumors are less aggressive notwithstanding the possibility of the estrogen acting as a growth stimulant. The inventors believe that over time the above-mentioned taboo will weaken or disappear, but in the meantime the invention has particular application to treating or preventing estrogen-independent breast cancer. In particular, the combination therapy of the invention is a good option for breast cancer survivors without any current evidence of cancer because the combination therapy should reduce the chances of metastases and possibly even reduce the growth of any undetected tumors. It should be borne in mind that anything that reduces the most aggressive type of breast cancer, as the below data corroborate, is relevant and important with respect to all breast cancer. Indeed, if the patient were to develop estrogen-dependent breast cancer in the presence of the instant HRT, the HRT would most likely keep the cancer responsive to tamoxifen—thus providing an additional benefit to the invention. Finally, although the inventors believe that there may be particular benefits associated with administration of natural hormones rather than synthetic ones, it is also believed that all of the estrogen and progesterone-receptor-binding compounds and compositions will work in the context of the invention, that is, in combination with melatonin administration. In summary, the inventors believe that a wide population of patients, including women, with all sorts of forms of breast cancer and particularly those in whom there is no breast cancer or in whom incipient breast cancer has not yet been diagnosed, will ultimately be helped dramatically and sometimes immeasurably by the treatments disclosed and claimed herein.

EXAMPLE 1

We studied the effects of the present combination therapy as follows. We chose a mouse model, MMTV-neu mice, which express the neu oncogene that mimics HER2+ breast cancer. In a population of mice, both melatonin and HRT were given orally to correlate with the dosage method in women, basing the dosing on diet based on the calories an average woman consumes daily, namely, 1800 kcal, but adjusting for the small size and metabolism of the mice. Estrogen+progestin HRT contained the bioidentical hormones 17β-estradiol ($E_2$) at the currently recommended dosage for women (0.5 mg/1800 kcal) and progesterone ($P_4$) at half of the recommended dose (50 mg/1800 kcal). For example, the daily mouse dose would be less than 500 mcg progesterone ($P_4$). Melatonin was provided in the drinking water at a concentration of 15 mg/L (dose equivalent to a 5 mg tablet for women) only during the night to supplement the normal nocturnal surge in endogenous melatonin. Using drinking water rather than food to administer melatonin allowed the mice continual access to the control and HRT diets, instead of just during the night (dark cycle).

Referring now to FIG. 1, survival curves are shown which represent the age of primary mammary tumor onset in weeks, on the x axis, and percent mammary tumor incidence on the y axis. FIG. 1a represents age of primary mammary tumor onset and incidence between control (C/V) vs. melatonin (C/M) groups, with C signifying no hormone administration, V signifying no melatonin administration, and M signifying melatonin administration. FIG. 1b represents control vs. HRT (HRT/V) groups, with C signifying no hormone administration, V signifying no melatonin administration, and with HRT signifying Hormone Replacement Therapy (in FIG. 1b, without melatonin, or "V"). FIG. 1c represents the results of HRT/V versus HRT/M administration (M=melatonin) and FIG. 1d represents the results of C/V versus HRT/M administration. The results for the tumor studies showed a multitude of effects using nocturnally administered melatonin in combination with HRT on mammary tumor latency, growth and progression. No change in body weight occurred as a result of the treatments. Melatonin alone did not modify the latency or incidence of mammary cancer in the neu mice (see FIG. 1a). As shown in FIG. 1b, the incidence and latency were not adversely affected by HRT alone, which is in marked contrast to the adverse effects reported in the 2002 Women's Health Initiative study. FIG. 1c represents HRT vs. HRT plus melatonin; FIG. 1d represents control versus HRT plus melatonin. The combination of melatonin with HRT resulted in a significant increase in latency and decrease in incidence when compared to control animals, as easily visible in FIG. 1d. For control animals, the incidence of mammary cancer was 44/57 (77%), 42/57 (74%) for melatonin-treated, 36/56 (64%) for HRT-treated and 30/51 (59%) for HRT/melatonin treated. These data suggest that the combined melatonin plus HRT therapy has preventive action on mammary tumor development both in neu mice and (concomitantly) in human subjects, particularly women patients, and the data substantiate the conclusion that the combined administration of HRT and melatonin gives new and unexpected results as illustrated in FIG. 1d.

EXAMPLE 2

Figure 2:
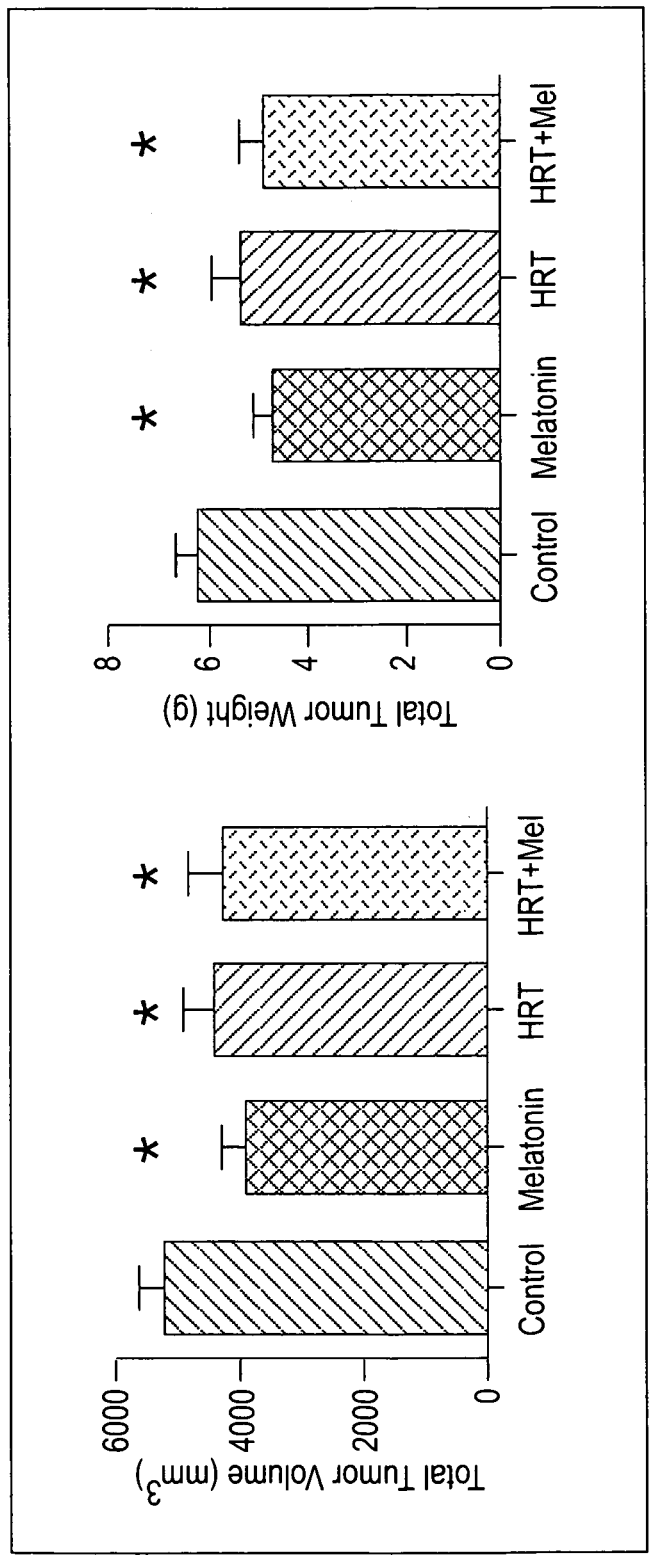
FIG. 2 is a bar graph showing decrease if any in total tumor volume in three groups of mice upon administration of melatonin, HRT, and HRT plus melatonin, in contrast with the fourth group of control mice.

As a result of the same study reported in Example 1, and with respect to tumor growth, melatonin, HRT, and combinations thereof showed a significant decrease in tumor weight and volume compared to control animals (FIG. 2). These data suggest that reduced tumor growth is a promising benefit of administration of all three active agents and in particular that the co-administration of melatonin with HRT improves the decreasing of total tumor volume compared to HRT given alone.

EXAMPLE 3

Figure 3B:
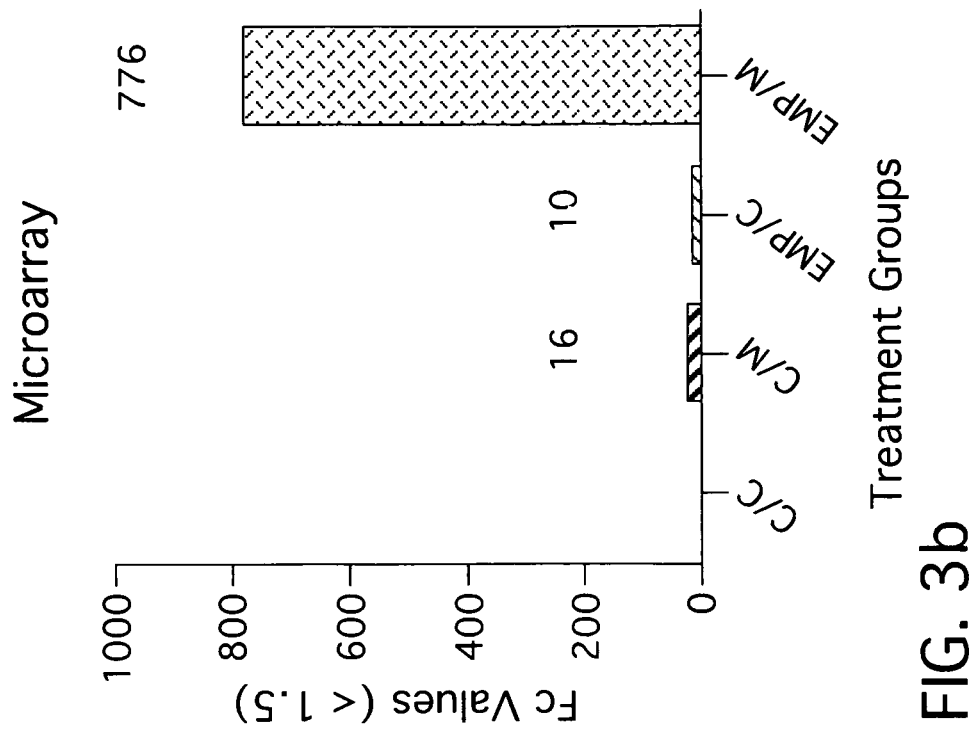
FIG. 3 is a bar graph showing the result that mice exposed to hormone replacement therapy with melatonin experienced dramatic change in RNA expression in the lower mammary gland.
Figure 3A:
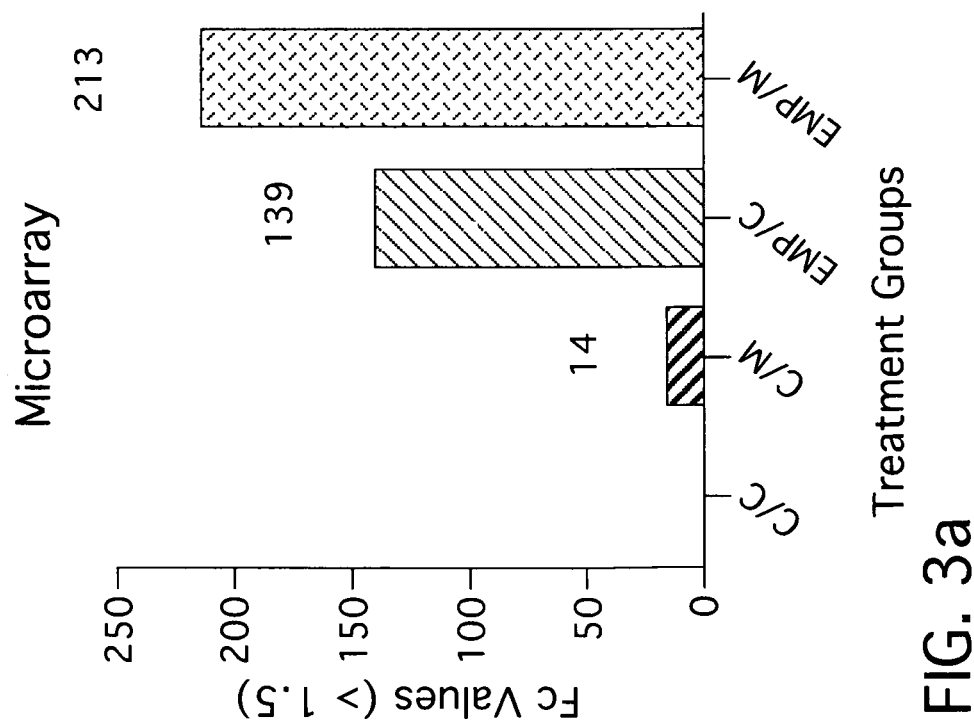

Mice exposed to hormone replacement therapy with melatonin, according to the present invention, experienced dramatic changes in RNA expression (both upregulation and downregulation) in the lower mammary gland as determined by microarray analysis. However, melatonin alone resulted in a limited number of RNA expression changes. FIG. 3 reports aggregated data regarding thousands of RNA fragments tested for over- or under-expression of more than one and one-half times more or less expression than in control, for mice treated with C/C (no hormone, no melatonin control), C/M (no hormone/melatonin), EMP/C (estrogen/mid progesterone (that is, half the recommended dose of progesterone, or 50 mg ($P_4$)) but no melatonin) and EMP/M (estrogen/mid progesterone (that is, half the recommended dose of progesterone, or 50 mg ($P_4$)) and melatonin). The y axes of FIG. 3a and FIG. 3a are different, and show that although many many RNA fragments or moieties (213) are upregulated upon administration of EMP/M (FIG. 3a), many many more RNA fragments or moieties (776) are downregulated by EMP/M (FIG. 3b). Moreover, the overwhelming preponderance of the downregulation occurs with EMP/M and not with either the hormone therapy or the melatonin therapy when administered without the other.

Although the invention has been described with particularity above, with special reference to specific materials and methods, the invention is only to be limited insofar as is set forth in the accompanying claims. As non-limiting examples, the active agents of the present invention may be added in suitable form (micronized, etc.) to a topical cream intended for application at night to the legs, arms, abdomen or even to the face. Women in particular in many cases are open to and even agreeable to the application of skin creams at bedtime and such a routine can enhance compliance with the inventive dosing regimen. Dosing can be metered by placing the cream-formulated ingredients in a metering dispenser, so that a single "pump" of the dispenser represents a defined dose; two pumps is double the first one-pump dose, and so on.

The invention as claimed is:

1. A method of suppressing Her2+ mammary cancer tumor development in a patient in need of said suppression, comprising administering in unit dosage form an estrogen, a progesterone-receptor-binding compound or composition, and melatonin, wherein said melatonin is administered to correspond with the sleep cycle of said patient and wherein said estrogen is 17β-estradiol, said progesteron-receptor-binding compound or composition is progesterone, and where said 17β-estradiol is administered via oral route of administration to said patient in the amount of 0.1-0.9 mg per day, said progesterone is administered via oral route of administration to said patient in the amount of 10-90 mg per day and further wherein said melatonin is administered via oral route of administration in a dose of between 1-9 mg per day.

* * * * *